United States Patent [19]

Ittel et al.

[11] 4,155,925
[45] May 22, 1979

[54] HEXAKIS- AND DIHYDRIDOPENTAKIS(PHOSPHITE ESTER)CHROMIUMS

[75] Inventors: Steven D. Ittel; Chadwick A. Tolman, both of Wilmington, Del.

[73] Assignee: E. I. Du Pont de Nemours and Company, Wilmington, Del.

[21] Appl. No.: 878,652

[22] Filed: Feb. 16, 1978

[51] Int. Cl.² .................................................. C07F 11/00
[52] U.S. Cl. .......................... 260/438.5 R; 585/277; 252/431 P
[58] Field of Search .............. 260/438.5 R; 252/431 P

[56] References Cited

U.S. PATENT DOCUMENTS

| | | | |
|---|---|---|---|
| 3,110,747 | 11/1963 | Mullineaux | 252/431 P X |
| 3,117,983 | 1/1964 | Matthews | 260/438.5 R X |
| 3,243,468 | 3/1966 | Clark et al. | 252/431 P |
| 3,346,608 | 10/1967 | Kutepow et al. | 252/431 P |
| 3,522,288 | 7/1970 | Drinkard et al. | 260/438.5 R X |
| 3,906,017 | 9/1975 | Middleton et al. | 260/438.5 R |
| 3,997,579 | 12/1976 | Jesson et al. | 260/439 R |

OTHER PUBLICATIONS

Mathieru et al., Inorg. Chem., vol. 11, pp. 1858-1861 (1972).
Libbey et al., J. C. S. Dalton (1974).
Timms, Advan. Inorg. Chem. Radiochem., 14, 121-171 (1972).
Timms, J. Chem. Educ., 49, 782 (1972).

*Primary Examiner*—Helen M. S. Sneed

[57] ABSTRACT

Hexakis(phosphite ester)chromiums of the formula

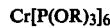

are prepared by chromium-atom evaporation and cocondensation with a phosphite ester. Dihydridopentakis(phosphite ester)chromiums of the formula

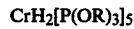

are prepared by hydrogenation of the corresponding hexakis(phosphite ester)chromiums. Both the hexakis- and the dihydridopentakis(phosphite ester)chromiums are useful as hydrogenation catalysts.

9 Claims, No Drawings

HEXAKIS- AND DIHYDRIDOPENTAKIS(PHOSPHITE ESTER)CHROMIUMS

BACKGROUND OF THE INVENTION

1. Field of the Invention

This invention relates to complexes of zero-valent chromium containing six phosphite-ester ligands and to related hydride complexes.

2. Description of the Prior Art

Zerovalent metal complexes of metals such as nickel, iron, and molybdenum containing only phosphite-ester ligands are known. For example, in U.S. Pat. No. 3,997,579 Jesson and Tolman disclose the preparation of pentakis(trimethyl phosphite)iron and related compounds by evaporating metallic iron in a high vacuum and cocondensing the iron atoms with trimethyl phosphite.

Mathieu and Poilblanc, Inorg. Chem., 11, 1858 (1972), report the preparation of hexakis(trimethyl phosphite)molybdenum by displacing the carbonyl ligands of hexacarbonylmolybdenum with trimethyl phosphite in the presence of ultraviolet radiation. They were not able to make this reaction go to completion with hexacarbonylchromium or hexacarbonyltungsten. At the end of the article they state: "Apparently in the trimethyl phosphite series a combination of steric and electronic effects prevents hexasubstitution for Cr and W but permits it for Mo."

Libby and Bancroft, J. C. S. Dalton, 87 (1974), at page 89, Column 2, note the work of Mathieu and Poilblanc and state that their preparation of [Fe{P(OMe)$_3$}$_6$]$^{2+}$ and the existence of [Co{P(OMe)$_3$}$_6$]$^{3+}$ "suggest that there is probably no steric reason for not anticipating" the preparation of hexakis(trimethyl phosphite)chromium "by some other route."

SUMMARY OF THE INVENTION

Hexakis(phosphite ester) complexes of zerovalent chromium and related dihydridopentakis(phosphite ester) complexes of chromium have now been prepared. The products of this invention are of the formula CrH$_{2n}$[P(OR)$_3$]$_{6-n}$, where n is 0 or 1 and R is primary or secondary lower alkyl, primary or secondary oxa(-lower alkyl), or primary or secondary lower alkyl substituted by a phenyl group on a carbon separated from the phosphorus-bonded oxygen by at least two other carbons.

DETAILED DESCRIPTION OF THE INVENTION

In the products of this invention the chromium is bonded to six phosphite-ester ligands through the phosphorus atoms or to five phosphite-ester ligands and two hydrogen atoms which are present as hydride ligands.

Lower alkyl is defined as alkyl of up to 8 carbons. Examples are methyl, ethyl, propyl, isopropyl, butyl, s-butyl, isobutyl, pentyl, neopentyl, hexyl, heptyl, isoheptyl, 2-ethylhexyl, and octyl.

An oxa(lower alkyl) group is a lower alkyl group in which a —CH$_2$— group has been replaced by —O—. Such groups are also known as alkoxyalkyl groups. Examples are 3-oxabutyl(2-methoxyethyl), 6-oxaoctyl(5-ethoxypentyl), and 2-oxahexyl(butoxymethyl).

Examples of phenyl-substituted lower alkyl groups are 3-phenylpropyl, 3-phenylbutyl, 4-phenylbutyl, and 8-phenyloctyl.

The preferred value of R is primary lower alkyl.

The hexakis(phosphite ester)chromium compounds are made by a metal-atom-evaporation process. This recently developed technique is described in detail by Timms in Advan. Inorg. Chem. Radiochem., 14, 121-171 (1972). By this technique, chromium metal is vaporized under high vacuum, and the walls of the surrounding vacuum chamber are cooled with liquid nitrogen. This allows the vapor of the phosphite ester ligand to be passed into the chamber while the chromium is evaporating and then be condensed on the cold walls so rapidly that high-vacuum conditions are maintained. Even with substantial rates of addition of the ligand, very little of it comes in contact with the hot chromium source or reacts with the chromium vapor species until the moment of condensation on the cold walls.

In the preparations by this technique, chromium is vaporized in a vacuum (usually between 0.01$\mu$ and 1$\mu$) from a crucible heated by passing an electric current (typically 60-100 amperes at 10-15 volts) through a molybdenum or tungsten wire coil, or by heating directly by an electron beam (typically 70-120 milliamperes at 10,000 volts). Apparatuses for vaporization by these two methods are shown on pages 132 and 136 of the Timms reference. Typical rates of vaporization are 0.1-5 g/hr. and preferably 1-3 g/hr.

The phosphite ligand to be reacted with the chromium is admitted to the high-vacuum chamber as a vapor from a magnetically stirred reservoir, at a rate such that the ligand:chromium mole ratio is between about 5:1 and 25:1, preferably about 10:1. For ligands of relatively low volatility, the reservoir and transfer line can be heated to give higher vapor pressure and higher feed rates. The walls of the reaction chamber on which cocondensation of chromium and ligand takes place are cooled with liquid nitrogen.

The dihydridopentakis(phosphite ester)chromium compounds can be made by reacting the hexakis(phosphite ester) complexes with hydrogen, for example by pressurizing with hydrogen at room temperature. They can also be prepared by reducing the hexakis(phosphite ester) complexes with an alkali-metal amalgam such as cesium amalgam.

Both the hexakis- and the dihydridopentakis(phosphite ester)chromiums of this invention are useful as catalysts for the hydrogenation of olefins.

EXAMPLES OF THE INVENTION

The following examples illustrate the products of the invention. All transfers and workups were carried out in an inert atmosphere, such as that supplied by argon or nitrogen.

In these examples metal-atom-evaporation syntheses were carried out in a modified version of the apparatus described by Timms in J. Chem. Educ., 49, 782 (1972). The pumping system consists of a 3-inch oil diffusion pump backed by a high-capacity, two-stage, mechanical vacuum pump, with a liquid-nitrogen-cooled trap between the reaction chamber and the pumping system. The heater for vaporization of the metal consists of a 5-ml alumina crucible with an integral tungsten filament (GTE Sylvania Emissive Products) suspended by two water-cooled electrodes. The crucible is powered by a 220-volt variac run through a step-down transformer capable of delivering greater than 60 amperes at 25 volts. The glass flask, which is immersed in liquid nitrogen during the synthesis, is 20 cm in diameter and 36 cm deep. It is connected to the metal head of the apparatus by a Viton ® fluoroelastomer "O" ring seal, and secured by a McCarter clamp.

Volatile phosphite ester ligands to be cocondensed with the metal atoms are stored in calibrated 200-ml cylinders sealed with screw-type high-vacuum stopcocks made of Teflon ® fluorocarbon resin. The vaporized ligands are carried to the apparatus through heated glass tubing and introduced into the reaction flask through a glass "shower head" sealed at the top by a ball joint. The ligand-introduction system is also connected to a mechanical vacuum pump and a source of argon for providing the entire apparatus with an inert atmosphere.

EXAMPLE 1

Hexakis(trimethyl phosphite)chromium

The resistance-heated crucible of the apparatus described above was charged with about 15 g of lump chromium metal. The glass flask was installed and the system was evacuated to less than $10^{-3}$ torr. The flask was immersed in liquid nitrogen, and 30 ml of pentane was condensed into the flask to coat the walls. Trimethyl phosphite was condensed into the flask at a rate of about 1 ml/min, and the voltage to the crucible was slowly increased over a period of minutes to give a total power of about 665 watts. Darkening of the flask walls, corresponding to the condensation of metal, was observed at this power. After 1.5 hours, the power was increased to about 775 watts. The run was stopped after another hour, at which point 176 ml of trimethyl phosphite had condensed into the reaction flask.

An additional 30 ml of pentane was condensed into the flask, and the flask was allowed to warm slowly toward room temperature. The added pentane caused the mixture to flow to the bottom of the flask at around $-120°$ C. (the approximate melting point of the pentane), and the mixture was stirred magnetically for 1 hr. The mixture was removed from the evaporator under a flow of argon and taken into a nitrogen-filled dry box. The mixture was filtered through degassed Celite ® diatomaceous earth and transferred to a round-bottomed flask, and volatiles were evaporated under vacuum. The sample was stored at $-78°$ C. overnight and then returned to the dry box, where the residual solids were extracted with pentane and the pentane extract was filtered again through diatomaceous earth. A small portion of the filtrate was set aside, and the remainder was treated with Darco ® activated carbon. Filtration and removal of volatiles under vacuum gave tacky solids, which were taken up in pentane. The mixture was filtered through degassed Woelm neutral grade alumina (Activity 1) and evaporated under reduced pressure to give hexakis(trimethyl phosphite)chromium as a yellow solid. The $^{31}P\{^1H\}$ and $^1H$ nmr spectra were single lines at 196.3 ppm and 3.6 ppm, respectively, consistent with the assigned structure.

Analyses were carried out on another sample, prepared in a similar manner and having identical nmr spectra. Its solutions had been filtered twice through diatomaceous earth, but not through carbon or alumina.

Anal. Calcd for $C_{18}H_{54}CrO_{18}P_6$: C, 27.15; H, 6.84; P, 23.34. Found: C, 27.01; H, 6.79; P, 23.59; C, 26.56; H, 6.70.

If trioctyl phosphite is substituted for trimethyl phosphite in essentially the foregoing process, hexakis(trioctyl phosphite)chromium will be formed. If tris(2-methoxyethyl)phosphite is used, the product will be hexakis[tris(2-methoxyethyl)phosphite]chromium. With tris(3-phenylpropyl)phosphite, hexakis[tris(3-phenylpropyl)phosphite]chromium will be produced. In each of these preparations, it would be advantageous to warm the reservoir, feed tube, and shower head for the phosphite ester appreciably above room temperature.

EXAMPLE 2

Dihydridopentakis(trimethyl phosphite)chromium

A solution of 2.39 grams of hexakis(trimethyl phosphite)chromium in about 30 ml of toluene was pressured with hydrogen at 20 psi and room temperature in a glass vessel for one hour. The solution was transferred to a nitrogen-filled dry box, and volatile materials were removed under reduced pressure. The residue was taken up in pentane, and the solution was chromatographed on degassed Woelm neutral-grade alumina (activity 1), with elution by pentane. The nearly colorless solution was evaporated under reduced pressure to give dihydridopentakis(trimethyl phosphite)chromium as an off-white solid. The $^1H$ nmr spectrum of the product displayed the expected resonances at 3.64 ppm (phosphite) and $-7.71$ ppm (hydride); $J_{PH}=53.3$ Hz (sextet).

Analyses were carried out on another sample, prepared in a similar manner and having an identical nmr spectrum.

Anal. Calcd for $C_{15}H_{47}CrO_{15}P_5$: C, 26.72; H, 7.03; P, 22.97. Found: C, 26.99; H, 7.08; P, 23.90; C, 26.87; H, 7.00.

If hexakis(trioctyl phosphite)chromium is substituted for hexakis(trimethyl phosphite)chromium in essentially the foregoing process, dihydridopentakis(trioctyl phosphite)chromium will be formed. If hexakis[tris(2-methoxyethyl)phosphite]chromium is used, the product will be dihydridopentakis[tris(2-methoxyethyl)phosphite]chromium. With hexakis[tris(3-phenylpropyl)phosphite]chromium, dihydridopentakis[tris(3-phenylpropyl)phosphite]chromium will be produced.

EXAMPLE 3

Hexakis(triethyl phosphite)chromium

The procedure was essentially that of Example 1, except that triethyl phosphite was used instead of trimethyl phosphite, the maximum power was about 874 watts for 1.5 hr, and the pentane solution of the product was filtered only once, through diatomaceous earth. The solution of hexakis(triethyl phosphite)chromium was evaporated under reduced pressure, during which process chromium metal precipitated. The residual material was found to be a mixture of triethyl phosphite and suspended chromium, formed by decomposition of the product during workup. The product can be isolated by working it up and storing it at lower temperatures.

EXAMPLE 4

Dihydridopentakis(triethyl phosphite)chromium

Triethyl phosphite and chromium were cocondensed essentially as in Example 3, except that the top power was about 821 watts for 2.25 hr. Hydrogen was admitted to the system to a pressure of 600 torr at $-196°$ C., after which the cooling bath was removed and the mixture was stirred for 24 hours. The mixture was transferred to a nitrogen-filled dry box and filtered through diatomaceous earth. Volatile materials were evaporated under reduced pressure, and the residue was extracted with a minimum amount of pentane. Filtration and removal of volatile materials again under reduced pressure gave dihydridopentakis(triethyl phosphite)chromium as a yellow solid. The product was stable at −40° C., but darkened above this temperature upon standing. The $^1$H nmr spectrum of the product contained characteristic resonances for coordinated triethyl phosphite and a hydride sextet at −7.60 ppm, $J_{PH}$=54.6 Hz.

As shown in the following Examples, the products of the invention are useful as catalysts for the hydrogenation of hexene.

EXAMPLE A

Use of Hexakis(trimethyl phosphite)chromium

A glass pressure vessel was charged with 0.0796 gram of hexakis(trimethyl phosphite)chromium, 10 ml of deaerated toluene, and 1.25 ml of hexene. The vessel was closed, evacuated, and pressured to about 25 psig with hydrogen. The system was heated with stirring at 25° C. for about 1:40 hr:min, at 60° C. for 1:20 hr:min, and at 90° C. for 2:55 hr:min. At 90° C. the originally clear yellow solution turned green, and a dark brown solid appeared. Gas-liquid chromatography of the liquid product showed that hexane had been formed.

EXAMPLE B

Use of Dihydridopentakis(trimethyl phosphite)chromium

The procedure of Example A was repeated with 0.0674 gram of dihydridopentakis(trimethyl phosphite)chromium as the catalyst. The system was kept at 25° C. for 2:10 hr:min, 60° C. for 2:30 hr:min, and 90° C. for 1:55 hr:min. Analysis by gas-liquid chromatography showed that hexane had been formed.

What is claimed is:

1. Phosphite ester complexes of chromium of the formula $$CrH_{2n}[P(OR)_3]_{6-n}$$

where
n is 0 or 1 and
R is primary or secondary lower alkyl, primary or secondary oxa(lower alkyl), or primary or secondary lower alkyl substituted by a phenyl group on a carbon separated from the phosphorus-bonded oxygen by at least two other carbons.

2. The phosphite ester complexes of claim 1 in which n is 0, said complexes being hexakis(phosphite ester)chromiums of the formula $$Cr[P(OR)_3]_6.$$

3. The hexakis(phosphite ester)chromiums of claim 2 in which R is lower alkyl.

4. The hexakis(phosphite ester)chromiums of claim 3 in which R is methyl.

5. The hexakis(phosphite ester) chromium of claim 3 in which R is ethyl.

6. The phosphite ester complexes of claim 1 in which n is 1, said complexes being dihydridopentakis(phosphite ester)chromiums of the formula $$CrH_2[P(OR)_3]_5.$$

7. The dihydridopentakis(phosphite ester)chromiums of claim 6 in which R is lower alkyl.

8. The dihydridopentakis(phosphite ester)chromium of claim 7 in which R is methyl.

9. The dihydridopentakis(phosphite ester)chromium of claim 7 in which R is ethyl.

* * * * *